(12) United States Patent
Keating et al.

(10) Patent No.: US 10,098,627 B2
(45) Date of Patent: Oct. 16, 2018

(54) DELIVERY SYSTEM

(71) Applicant: Neosurgical Limited, Dublin (IE)

(72) Inventors: Ronan Keating, Moycullen Village (IE); Gerard Rabbitte, Tuam (IE)

(73) Assignee: NEOSURGICAL LIMITED, Galway (IE)

( * ) Notice: Subject to any disclaimer, the term of this patent is extended or adjusted under 35 U.S.C. 154(b) by 87 days.

(21) Appl. No.: 14/784,144

(22) PCT Filed: Apr. 17, 2014

(86) PCT No.: PCT/EP2014/057970
§ 371 (c)(1),
(2) Date: Oct. 13, 2015

(87) PCT Pub. No.: WO2014/170462
PCT Pub. Date: Oct. 23, 2014

(65) Prior Publication Data
US 2016/0051247 A1   Feb. 25, 2016

(30) Foreign Application Priority Data

Apr. 17, 2013  (GB) .................................. 1306981.0

(51) Int. Cl.
*A61B 17/04* (2006.01)
*A61B 17/34* (2006.01)
*A61B 17/00* (2006.01)
*A61B 19/00* (2006.01)
*A61B 90/00* (2016.01)

(52) U.S. Cl.
CPC ...... *A61B 17/0401* (2013.01); *A61B 17/3468* (2013.01); *A61B 17/3496* (2013.01); *A61B 2017/00876* (2013.01); *A61B 2017/0403* (2013.01); *A61B 2017/0409* (2013.01); *A61B 2017/0445* (2013.01); *A61B 2017/0464* (2013.01); *A61B 2019/481* (2013.01); *A61B 2090/08021* (2016.02)

(58) Field of Classification Search
CPC ............ A61B 17/3494; A61B 17/3496; A61B 2017/0409; A61B 2017/0445
See application file for complete search history.

(56) References Cited

U.S. PATENT DOCUMENTS

| | | | |
|---|---|---|---|
| 6,270,484 B1 * | 8/2001 | Yoon ................... | A61B 17/3494 604/264 |
| 2002/0161387 A1 * | 10/2002 | Blanco ............... | A61B 17/3496 606/185 |
| 2002/0188301 A1 | 12/2002 | Dallara et al. | |
| 2003/0216743 A1 * | 11/2003 | Hoffman ............ | A61B 17/0401 606/99 |
| 2004/0193217 A1 * | 9/2004 | Lubbers ............. | A61B 17/0401 606/232 |
| 2008/0140093 A1 | 6/2008 | Stone et al. | |
| 2009/0105743 A1 * | 4/2009 | Chu ................... | A61B 17/0469 606/185 |

(Continued)

FOREIGN PATENT DOCUMENTS

WO   97/07743 A1   3/1997

*Primary Examiner* — Alexander Orkin
(74) *Attorney, Agent, or Firm* — Schwabe Williamson & Wyatt, PC (57) ABSTRACT

A delivery system is described. The system includes an integrated shield which is used to selectively cover a needle end portion of the device.

11 Claims, 9 Drawing Sheets

(56) References Cited

U.S. PATENT DOCUMENTS

2010/0130989 A1     5/2010  Bourque et al.
2010/0324357 A1*   12/2010  Chu .................. A61B 17/0401
                                                            600/37
2014/0228863 A1*    8/2014  Watschke ........... A61B 17/0401
                                                            606/139

* cited by examiner

DELIVERY SYSTEM

FIELD OF THE INVENTION

The present invention relates to a delivery system and in particular to a delivery system used in surgical procedures. The invention more particularly relates to a delivery system that incorporates a sharpened tip which is operably used to ease the passage of components of the system through the abdominal wall. The invention more particularly relates to a delivery system that incorporates a a shield which is biased relative to the sharpened tip so as to operably cover the tip subsequent to passage of the tip through the abdominal wall.

BACKGROUND

Within the context of laparoscopic surgical procedures it is known for the surgeon to operably place instruments into the abdominal cavity and operate those instruments with limited visualisation. The instruments are presented into the cavity through ports and are then manipulated by the surgeon through the ports. Such surgical procedures use delivery systems both during and after the actual laparoscopic surgical event. During the surgical event a delivery system may be used to delivery an anchor to effect an anchoring of one or more surgical instruments relative to the surgical site. After the surgical event there is a need to effect a closure of the surgical wound and a delivery systems may be usefully employed to effect a delivery of suture to the site.

In both scenarios an instrument having a sharpened tip is used to penetrate the abdominal wall and provide access within the abdominal cavity. Use of the sharpened tip advantageously allows the surgeon to use the instrument itself to concurrently cut the necessary tissue to facilitate its passage through the abdominal wall. Unfortunately once inside the abdominal cavity the presence of the sharpened tip can cause difficulties as it can accidentally nick or cut tissue or organs. This is particularly the case in laparoscopic surgery where the surgeon has limited visualisation of the end of the instrument once it is within the abdominal cavity.

These and other problems are also found in non-laparoscopic surgical techniques.

SUMMARY

These needs and others are addressed in accordance with the present teaching which provides a delivery system for use as part of laparoscopic surgical procedures. In one configuration delivery system is used for delivery of an anchor for anchoring purposes during a surgical procedure. In another configuration the delivery system is useful for provision of suture.

These and other features of the present teaching will be better understood with reference to the drawings which follow which are provided to assist in an understanding of the present teaching and are not to be construed as limiting in any fashion.

BRIEF DESCRIPTION OF THE DRAWINGS

The present teaching will now be described with reference to the accompanying drawings in which.

DETAILED DESCRIPTION OF THE DRAWINGS

The teaching of the present invention will now be described with reference to exemplary embodiments thereof which are provided to assist with an understanding of the invention and are not to be construed as limiting in any way. It will be appreciated that modifications can be made to the exemplary arrangements which follow without departing from the scope of the invention which is only to be limited insofar as is deemed necessary in the light of the appended claims.

Within the context of the present teaching a delivery system advantageously allows a surgeon to deliver specific components within an abdominal cavity of the patient. It will be appreciated that the following discussion regarding the specifics of the abdominal cavity and abdominal wall should not be construed as limiting in that a system provided in accordance with the present teaching may be used with other types of tissue including but not limited to organs, bones or the like. The use of a delivery system per the present teaching can be used for one or more of anchoring laparoscopic surgical equipment, assisting in the moving of internal organs to allow a surgeon access to a surgical site, or closure of a wound post completion of a surgical procedure.

In such a latter configuration, where an anchor is coupled to suture such that as the suture is passed through the abdominal wall and is held within the wall by the anchors that will remain deployed within the abdominal cavity, a subsequent tightening of the sutures will cause the sides of the incision, or break in the abdominal cavity to be brought together to close the wound. The adoption of such a technique will advantageously require the use of bioabsorbable anchors, as the anchors will remain within the abdominal cavity during the healing process prior to their ultimate disintegration.

In a further embodiment of a delivery system used as an anchor delivery system, the anchors may be made from a ferromagnetic material so that a magnet could be passed down a trocar and the anchors would be attracted to and adhere to the magnet, allowing them to be drawn out through the trocar. The advantage of this approach is that direct visualisation may not be necessary. However, the anchors would need to be removed prior to tying the suture in a loop. Alternatively the anchors may be themselves magnets and a ferromagnetic pick up device could be employed through the trocar to pick up the anchors.

In accordance with an aspect of the present teaching related to an anchor delivery system, an anchor is coupled to the suture. The anchor may then be delivered to the surgical site through co-operation of the anchor with a driver tool. The driver engages with the anchor and is then used to deliver the anchor and its associated suture through to the abdominal cavity. A tensioning of the suture will then allow for a retraction of the anchor against an inner part of the abdominal wall, where it then provides an anchoring function.

The suture/anchor assembly may consist of a length of bioabsorbable suture attached to a length of bioabsorbable tubing in one embodiment such that the assembly is t-shaped. The suture may be a braided suture made from a bioabsorbable polymer such as PGA for example. For fascial layer closure a USP size 0 suture is preferred. This material is ideally suited to an application where the suture maintains approximately 50% of its strength after two weeks. However it will be appreciated that the suture material may be changed depending on strength or mass loss requirements of the specific application.

The driver may be used in combination with a needle guide channel such as those described in our co-pending application U.S. Ser. No. 13/975,599, the content of which is incorporated herein by reference. As described therein, in use, when the driver is presented into a needle entry port it moves within the channel until such time as it meets with the anchor that is located within the channel. It then drives the anchor through the channel until it exits through an exit port where it extends into the abdominal cavity.

In this configuration, to allow the driver to pass through an arcuate needle channel, it is desirably at least partially flexible.

U.S. Ser. No. 13/688,005, the content of which is incorporated by way of reference shows example of anchors that may be employed within the present teaching. FIG. 1 of the instant application illustrates how one such anchor could be coupled to a driver, per the present teaching.

In the example of FIG. 1 which illustrates use of a delivery system in accordance with the present teaching for delivery of an anchor, a delivery system 100 comprises a driver 110 which cooperates with an anchor 120. The anchor 120 is substantially hollow so as to allow presentation of the driver 110 into an inner volume of the anchor 120. In this way the anchor 120 will be arranged collinearly with the longitudinal axis of the driver such that a presentation of the driver through the abdominal wall—or a guide channel provided in a cooperating device—will direct the anchor in the same direction as a leading end 130 of the driver. The leading end tapers to a pointed extremity defining a sharpened tip. The sharpened tip 130 of the driver extends through the anchor, such that the driver presents a piercing leading surface that will operably extend beyond the body of the anchor and which on delivery of the anchor to the abdominal cavity can be withdrawn from the anchor, leaving the anchor in situ.

Figure 2:
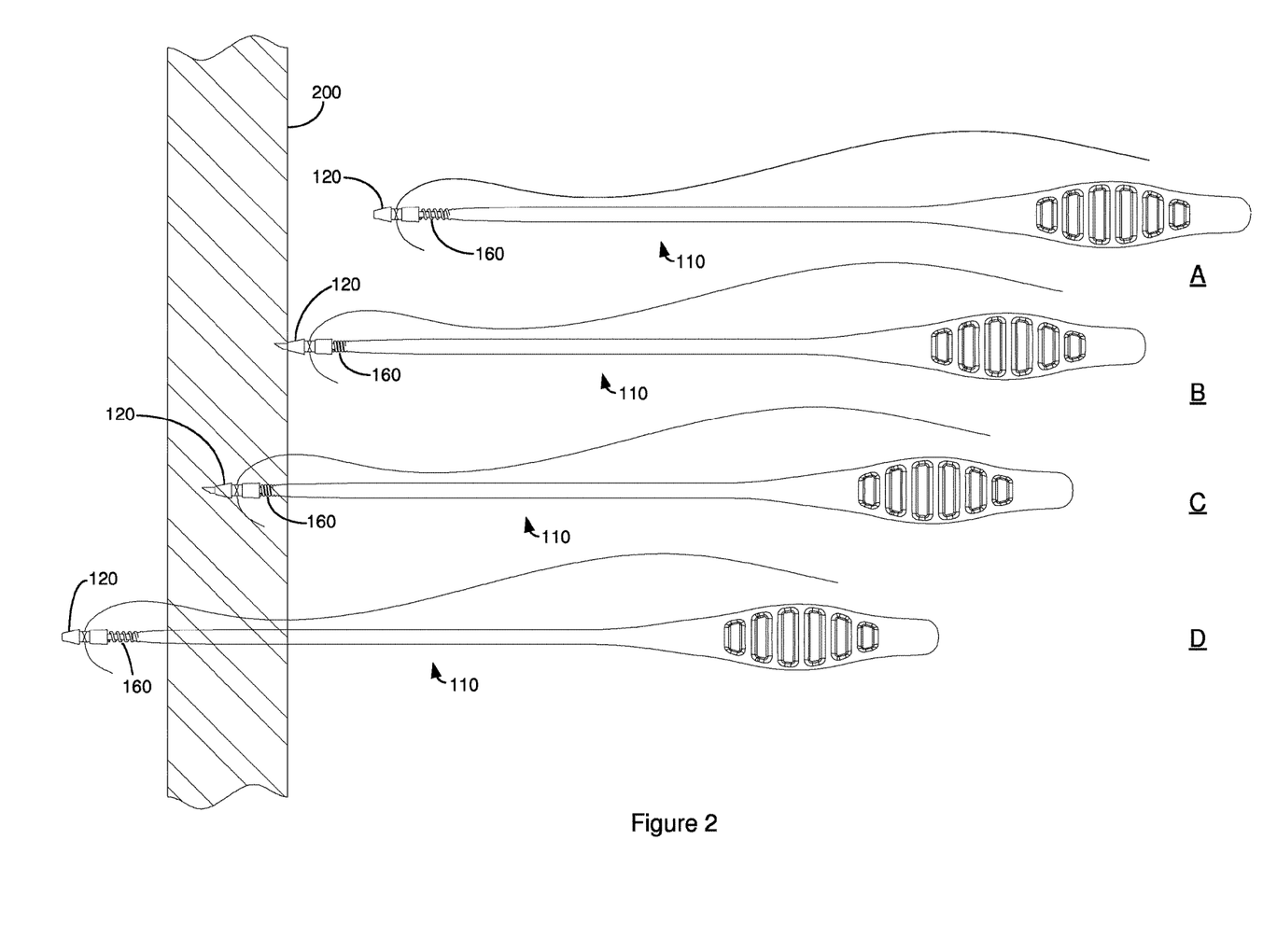
FIGS. 2A through 2D show the system of FIG. 1 as it is presented to, enters into, passes through and exits an abdominal wall in accordance with the present teaching.
FIGS. 2E through 2G show the system of FIG. 1 as it is presented to, passes through and exits an abdominal wall in a curved path in accordance with the present teaching.

It will be appreciated that by providing a hollow anchor, once the driver has engaged with the anchor it may then be used to drive the anchor forwardly. In this way and as shown in FIG. 2, pushing the driver forwardly effects a corresponding movement of the anchor through and into the abdominal cavity. When the anchor is delivered to the abdominal cavity and the driver is being withdrawn from the anchor, the anchor will disengage from the driver, which may then be withdrawn from the abdominal cavity.

As discussed above the driver projects through the anchor such that the anchor is located on the driver between a tip defined at the end of a driver needle end portion and a main body portion 140. This tip of the needle end portion is desirably sharpened to allow a piercing of the abdominal wall as necessary. The length and geometry of the needle end portion and its associated tip may vary. FIG. 5A shows an example of such an alternate needle geometry, whereby the tip portion of the needle is conical 180. In addition FIGS. 5B to 5D illustrate alternate anchor geometries. In these Figures a series of three blades or cutting wings 170 are positioned along the leading portion of the anchor 150, instead of the smooth conical geometry previously disclosed. Such features could be advantageously employed to facilitate cutting and separation of the fascia during a passage of the anchor through the fascia layer. In this way the anchor and tip of the needle end portion may be configured to cooperate to facilitate the introduction of the anchor into the abdominal cavity. While disclosed here as being three wings which run longitudinally down the conical section, it should be understood that these illustrations are not limiting, and that the number of wing could vary, as could the geometry. Additionally, the cutting wings are not limited to being orientated in a longitudinal direction, and a variety of other geometrical configurations such as helical may also be provided. The addition of such cutting wings is not limited to the leading portion of the anchor 150, but may also be applied to a distal portion of the anchor 190.

In another configuration the driver could be manufactured from triangular or square stock which has a ground needle edge. The external surface of the driver would therefore have a non-smooth profile. By providing the shield or anchor with a corresponding interior profile it is possible to accurately couple the shield and driver together—the exterior profile of the driver matching the interior profile of the shield. In such an implementation it is possible to accurately align the shield relative to the driver and this could be usefully employed in circumstances where the shield incorporates cutting features provided in its exterior surface. These cutting surfaces could be aligned with the faces of the needle to provide a smooth transition between the needle tip and the anchor.

The driver may be constructed from a single diameter wire with a ground needle tip, or may be centreless ground to a number of different profiles, which could be a series of stepped diameters and tapered sections or any combination thereof. This would facilitate optimisation of the stiffness profile of the driver.

An end surface 150 of the anchor may also include a chamfered outer surface which also facilitates the presentation of the anchor through the abdominal wall. It will be appreciated that as the driver is presented through the abdominal wall, the pressure on the leading surface 150 will increase and will push the anchor towards the main body portion 140 of the driver, until such time as the inner diameter of the anchor is greater than the outer diameter of the driver, at which time movement rearwardly of the anchor is prevented.

Figure 1A:
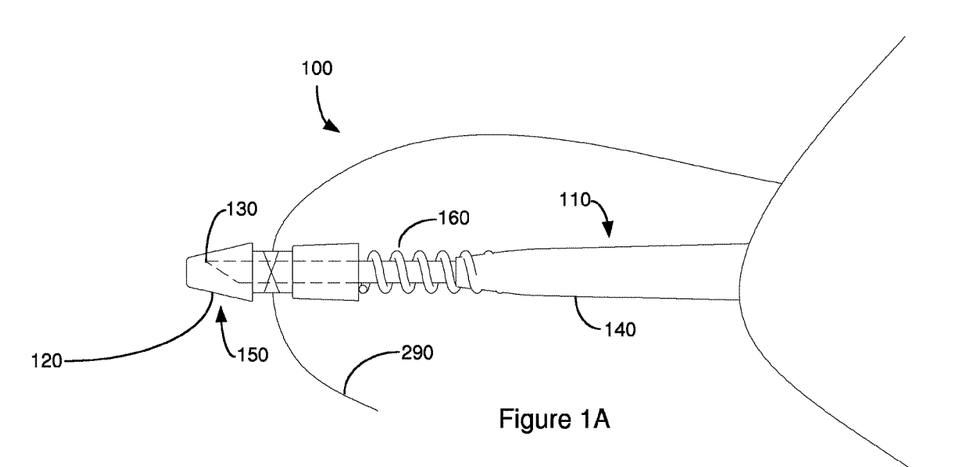
FIGS. 1A and 1B show a surgical delivery system in two modes of operation in accordance with the present teaching.
Figure 1B:
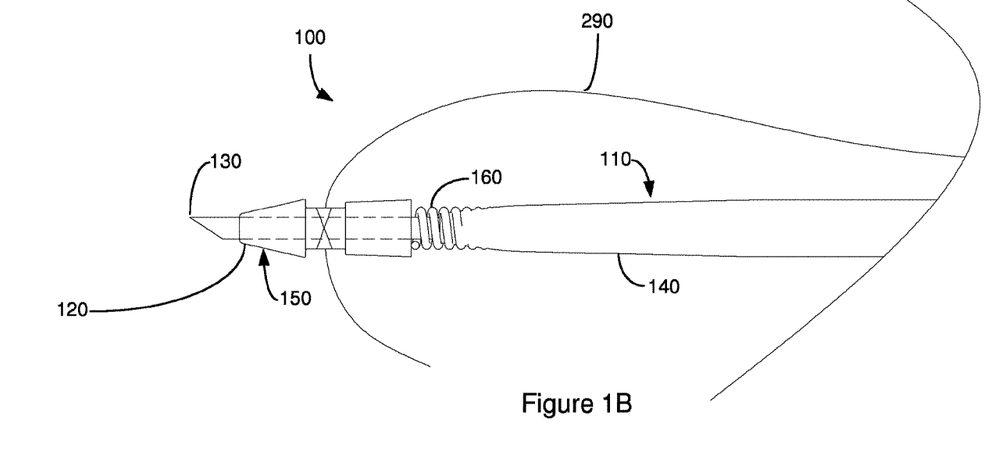

In accordance with the present teaching, the anchor is operably biased towards the driver needle end portion 130 such that in the absence of a force acting on the anchor away from the needle end portion 130, the anchor will tend to move forwardly along the driver in a direction towards the needle end portion 130. In the exemplary arrangements of FIGS. 1 and 2, this bias is provided by contact of the anchor with a spring 160. The spring is located proximal to the anchor and is moveable between a relaxed non-compressed and an actuated compressed state. In the relaxed state, an example of which is shown in FIG. 1A, the spring is extended and through its contact with the anchor 120 causes the anchor 120 to extend over and shield the needle end portion 130. The sharpened needle end portion 130 is thereby retained within the body of the anchor and cannot therefore come into inadvertent contact with other elements such as organs or body tissue.

In a compressed state, the anchor is forced through application of an external force onto the anchor in a direction away from the needle end portion 130. The tip 130 protrudes through the anchor (FIG. 1B) so as to project and provide a sharpened contact surface. This causes the spring to compress upon itself—shown in FIG. 1B as reducing the length of the spring relative to that shown in FIG. 1A. In accordance with physical principles (Hooke's Law) the force required to effect this compression is dependent on characteristics of the spring and thus a spring of suitable characteristics can be judiciously selected dependent on the specifics of the environment within which the device will operate.

FIG. 2 shows the various stages of movement of the anchor relative to the needle end portion 130. In the example of FIG. 2A, the driver 110 is coupled to the anchor 120 and no external force is biasing the anchor 120. In this state, the force effected by the spring 160 onto the anchor causes the anchor to shield the tip of the needle end portion 130.

In the example of FIG. 2B, the driver is presented to an abdominal wall 200. Contact of the abdominal wall against the end surface 150 of the anchor 120 generates a force in a direction opposite to that of the spring 160. Once that force is greater than the biasing force generated by the spring it causes the anchor to compress against the spring 160 so as to move the spring to its compressed condition. This force also allows the tip of the needle end portion to pass out from the shield that is provided by the anchor 120 such that the sharpened tip 130 of the needle end portion projects beyond the end surface 150 of the anchor 120 and facilitates the entry of the driver into the abdominal wall 200.

During the passage of the driver through the abdominal wall 200 continued pressure on the surface of the anchor retains the biasing force onto the anchor in the direction away from the needle end surface 130—FIG. 2C.

Once the driver end has passed into the abdominal cavity 210, there is no longer any external force acting on the anchor which is therefore only biased by the spring 160. The anchor therefore moves in a direction towards the needle end portion 130 and shields the needle end portion—FIG. 2D.

Use of the device as illustrated in FIGS. 2A to 2D shows the driver being driven straight through an abdominal wall. There may be scenarios where a driver is presented through an abdominal wall in a curved or tortuous path as illustrated in FIG. 2E and 2G, where the driver is used with a guide 600 which has an arcuate path. While not shown in FIGS. 2E-2G it will be appreciated that this guide may be used with a cooperating surgical device such as a trocar, the trocar providing resistance to the guide during presentation of the guide into the abdominal wall.

Many shielding devices work by housing a spring in the handle of the device, which is directly linked to the distal end of the device. However, in a scenario where the shaft potion 140 is curved, transmission of a biasing force from the handle portion 360 to the anchor 120 may inhibited by frictional forces. The device of FIGS. 1 and 2 are particularly advantageous in this regard, as the biasing force is located at the distal end of the device, adjacent to the shield, which enable it to function in a curved path.

There are many ways in which to achieve retention of the spring relative to the driver and the anchor. For example it is possible to attach the spring by overmoulding the spring onto the driver or by simple use of an adhesive.

It will be appreciated that the examples of FIGS. 1 and 2 are specific to an anchor delivery system where the driver is received through the anchor and the anchor is moveable over the sharpened needle end portion to selectively shield the sharpened needle end portion.

Figure 3:
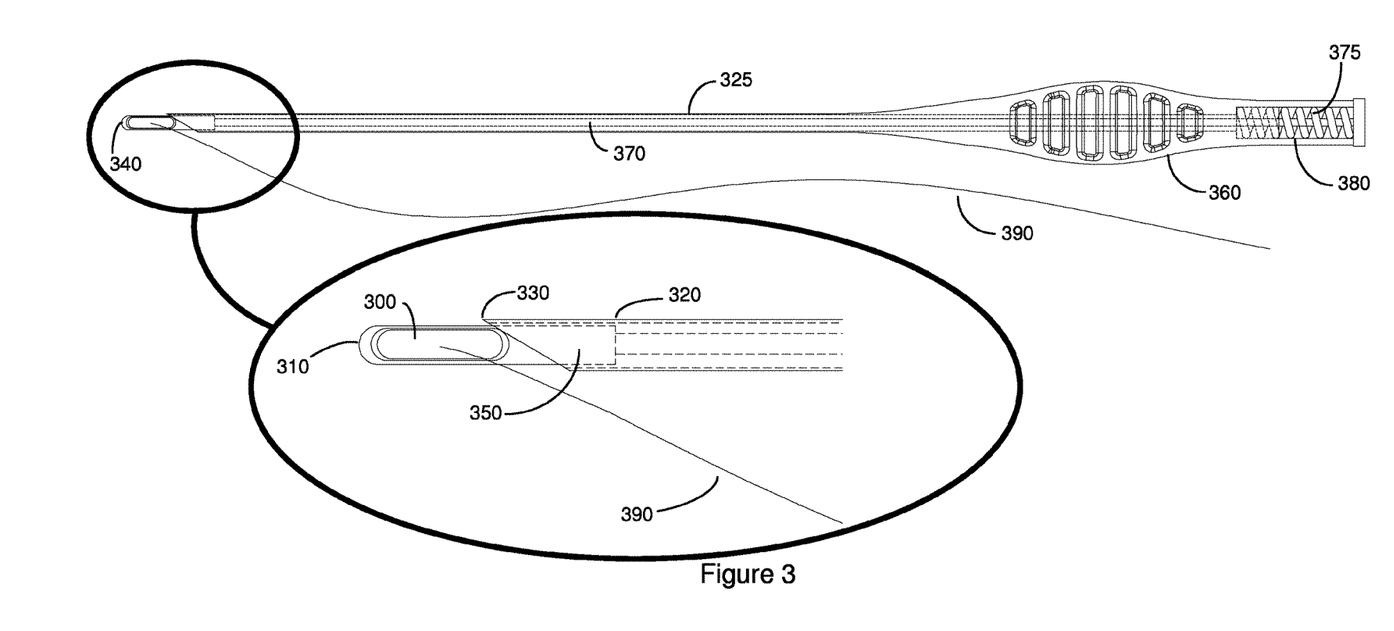
FIG. 3 shows another example of a suture delivery system in accordance with the present teaching.

FIG. 3 shows another example where an anchor 300 may be loaded into a receiver 310 that is moveable within a shaft 320 of the driver 325. The receiver is provided with a blunt end surface 340. Similarly to that described with reference to FIGS. 1 and 2, the driver comprises a sharpened needle end portion 330. Differing from the previous example, in this arrangement the driver comprises a hollow portion 350 within which the receiver/anchor are moveable. Similarly to that described above, the delivery system comprise an integrated shield which is moveable relative to the sharpened needle end portion 330 so as to provide periods of time when the end portion is shielded and cannot therefore inadvertently nick or otherwise come into contact with tissue or body organs. In this example, the integrated shield is moveable retracts into a hollow driver whereas in the first example the driver is moveable within the hollow shield.

In this example, and similarly to that described above, the shield is also resiliently biased forwardly so as to normally project beyond the sharpened tip of the needle end portion. Whereas in FIGS. 1 and 2, this biasing force was caused by locating a spring adjacent to the end of the driver, in this example a spring 375 is decoupled from the end of the driver and is instead located within a head region 360 of the driver 325. The force exerted by the spring is coupled to the shield 310 by a pin 370 that extends through the driver 325. The diameter of the pin 370 is desirably less than the diameter of the internal bore of the driver so as to allow a flexing of the driver without compromising an ability of the pin 370 to transmit the force generated by the spring onto the receiver shield arrangement. Such a configuration is advantageous in that it allows the use of the driver across bends or through a tortuous anatomical path.

In the arrangement of FIG. 3, a window 380 is provided in the head region 360 and allows a visualisation of the state of the spring 375. The portion of the spring that is normally not visible through the window—as the spring is in its normal non-compressed state—may be painted or otherwise provided with a visual indicator to alert the operator when the spring is moved to its compressed actuated state—the visual indicator will come into the window and be visible to an operator.

The anchor is desirably shaped, in this arrangement, to be received into the receiver 310. The mutual dimensions of the two are desirably selected such that the anchor may be controllably displaced from the receiver through use of a deployment pin or a simple rotation of the two to allow gravity effect a separation. By coupling the anchor to suture 390 it is possible to control the movement of the anchor once it has been displaced away from the delivery system.

Figure 4:
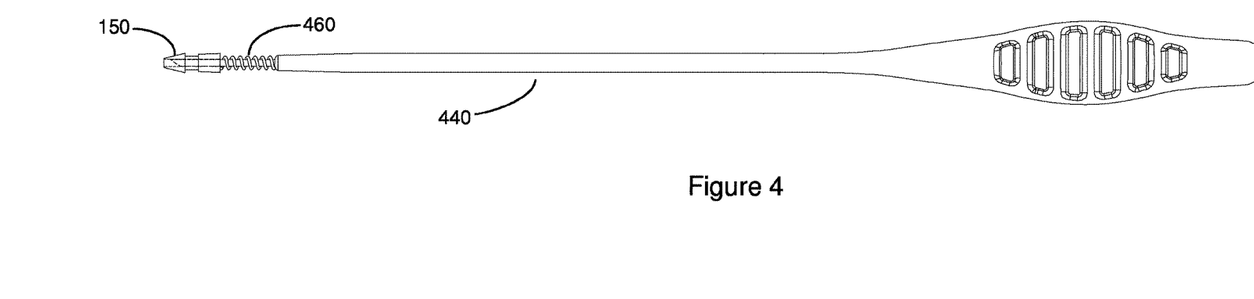
FIG. 4 is another example of a suture delivery system.

FIG. 4 shows another example of a delivery system, in this example the driver 440 is fabricated from steel and is provided with a welded spring 460 proximal to the anchor end 150.

Figure 5:
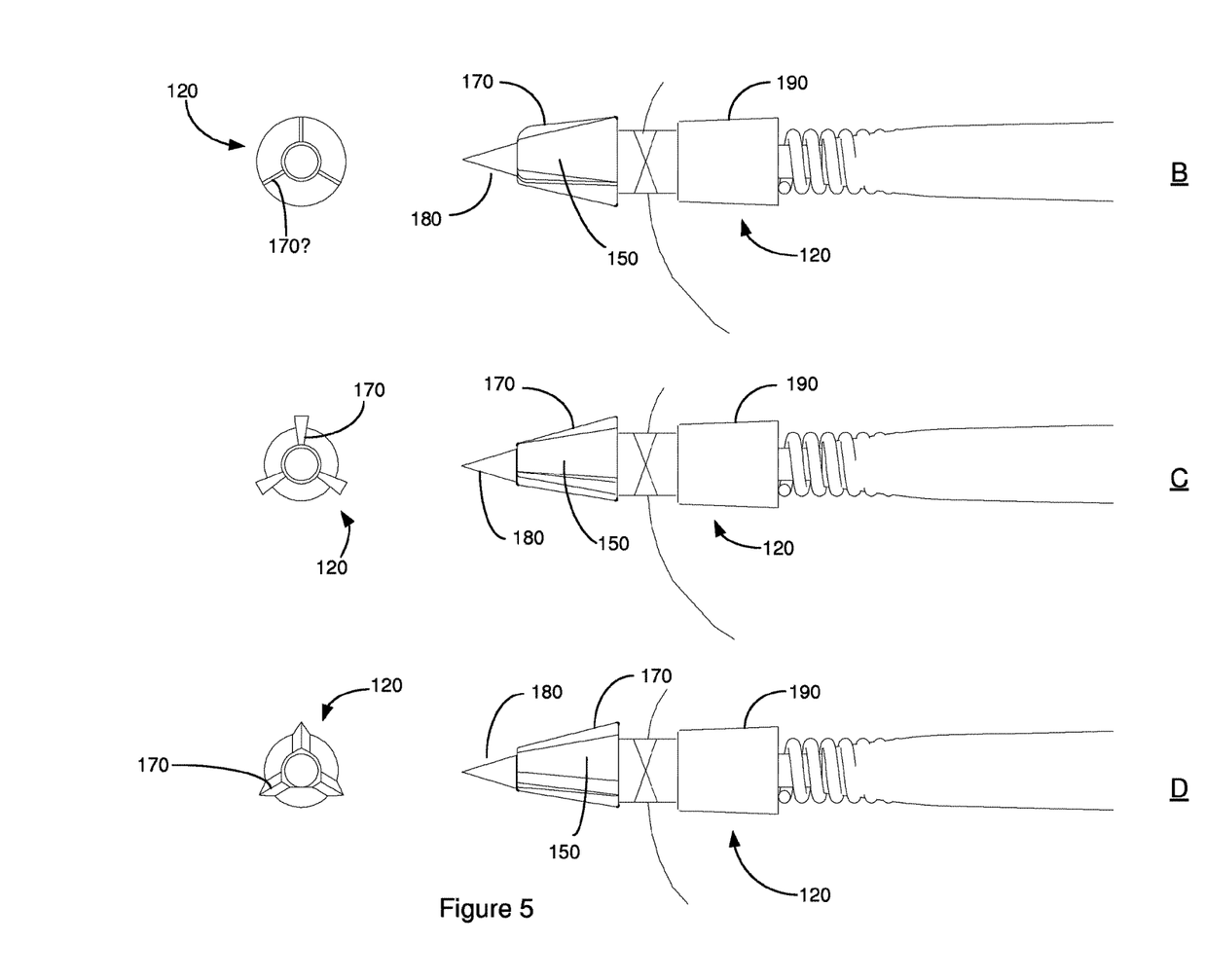
FIG. 5A shows an isometric view of a needle tip and anchor at the end of a driver.
FIG. 5B-5D shows plan and end views of alternate geometries of needle tips and anchors to that of 5A.
Figure 5A:
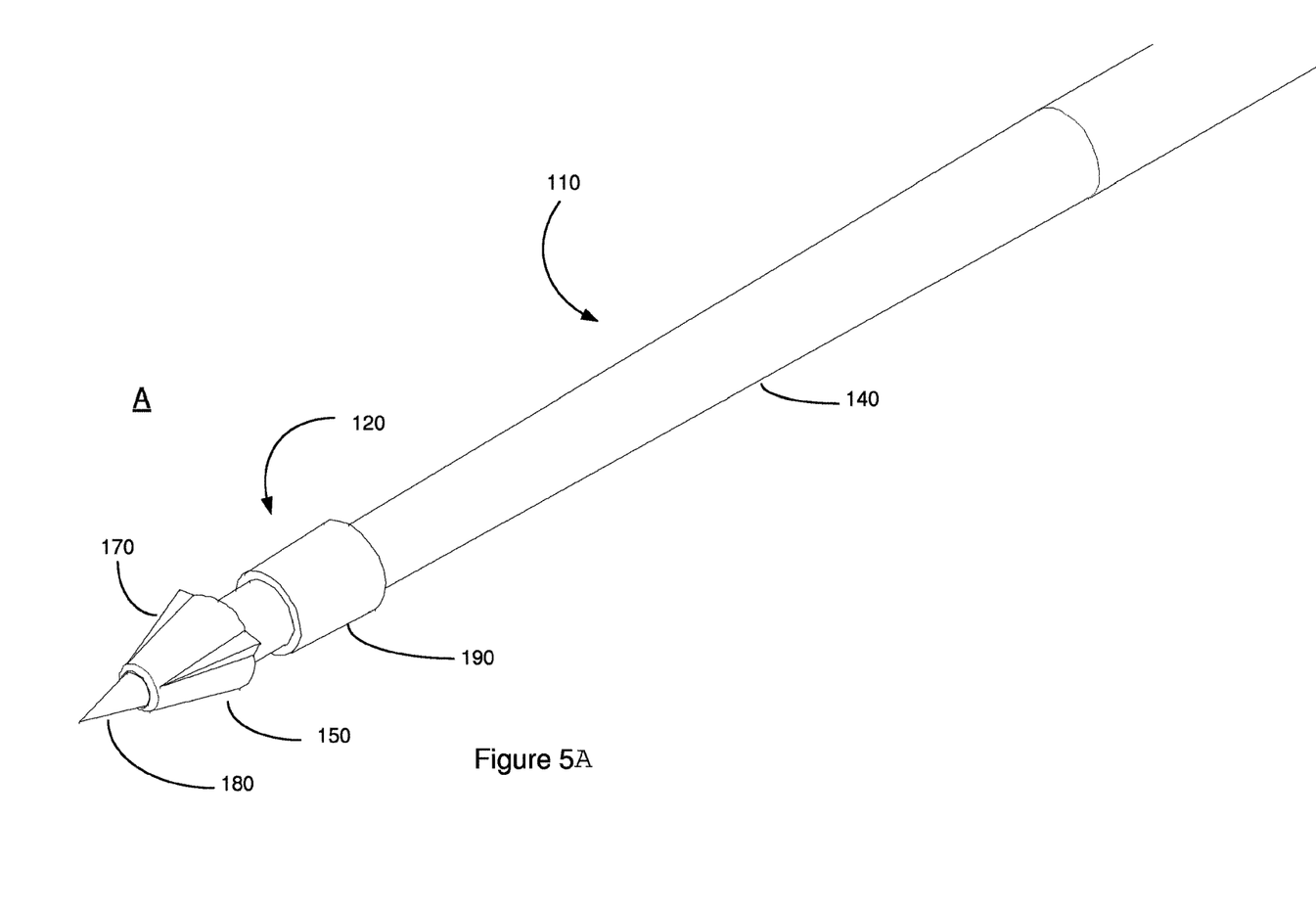
Figures 6A, 6B:
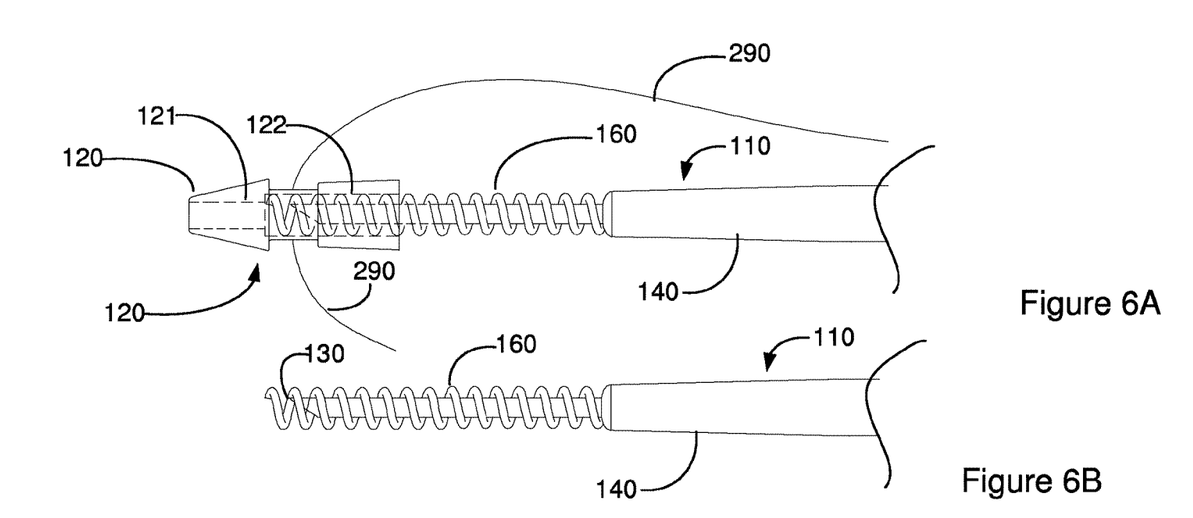
FIG. 6A-6D shows alternate geometries of a suture delivery system provided in accordance with the present teaching.
Figure 6C:
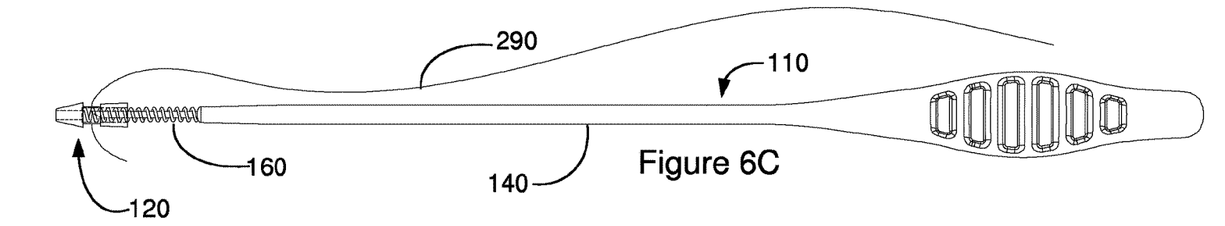
Figure 6D:
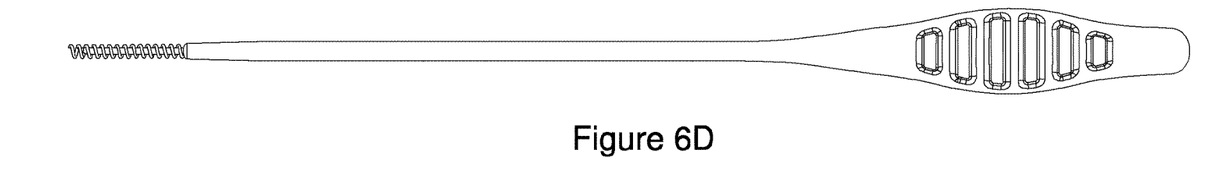

FIG. 6 shows a modification to the arrangement of FIGS. 4 and 5. In this arrangement the spring 160 is again provided proximal to the tip 130. As shown in FIGS. 6A and 6B, the spring has a normal relaxed position where it extends beyond the tip 130. On presentation of an anchor 120 onto the driver 110, the spring 130 is received into an interior portion of the anchor. In this way at least a portion of the spring is encapsulated within the anchor 120. When the driver is then presented to the abdominal wall the anchor 120 compresses against the spring 160 causing the spring to contract back towards the main body portion 140 of the driver. The anchor in this configuration has a tip or end portion 121 providing a chamfered end surface. Similarly to that described before, the sharpened tip 130 of the driver will project during passage of the anchor through the abdominal wall beyond the end portion 121 of the anchor. The chamfered end surface will assist in the delivery of the driver through the abdominal wall.

On receipt of the anchor into the abdominal cavity, the forces that causes the anchor to compress the spring are no longer present. The spring will therefore tend to its relaxed configuration. As part of this relaxation, the end portion 121 will firstly move away from the main body 140 of the driver, and will shield the sharpened tip-as shown in FIG. 6A. Retraction of the driver out of the abdominal cavity will result in the anchor 120 completely detaching from the forcing the anchor away from the driver 110. As a result the anchor will remain the abdominal cavity.

The anchor in this configuration comprises the end portion 121 and a trailing portion 122 which are separated by a step. The step provides a seat or coupling surface for suture 290. By coupling the suture to a mid-portion of the anchor, the anchor will tend to hang from the suture and adopt a T-bar configuration during tensioning of the suture.

In another application, the delivery system is used to deliver anchors into the abdominal wall. Such applications may require the deployment of the anchor from within the abdominal cavity. In this way the driver will be used to drive anchors outwardly from the abdominal cavity towards the outer surface of the abdominal wall. The presentation of the anchor into the abdominal wall causes the anchor to force the spring towards the body 140 of the driver and allows the sharpened tip to project through the end portion of the anchor and assist in penetration into the abdominal wall. Differing from the application just described, the driver is not presented fully through the abdominal wall, but instead once the anchor has been delivered a sufficient distance into the wall, the driver is retracted. The trailing surface 122 of the anchor provides an end surface that will abut against the tissue of the abdominal wall and assist in separation of the anchor form the driver. On complete separation and subsequent tensioning of suture 290, the anchor will change orientation within the abdominal wall to adopt a T-bar configuration.

Figures 7A, 7B:
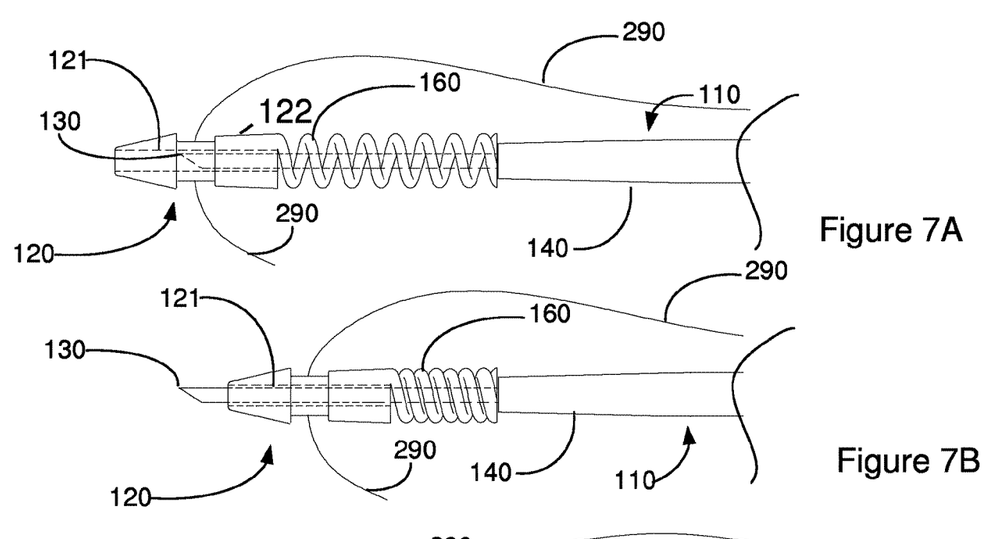
FIG. 7A-7D shows alternate geometries of a suture delivery system provided in accordance with the present teaching.
Figure 7C:
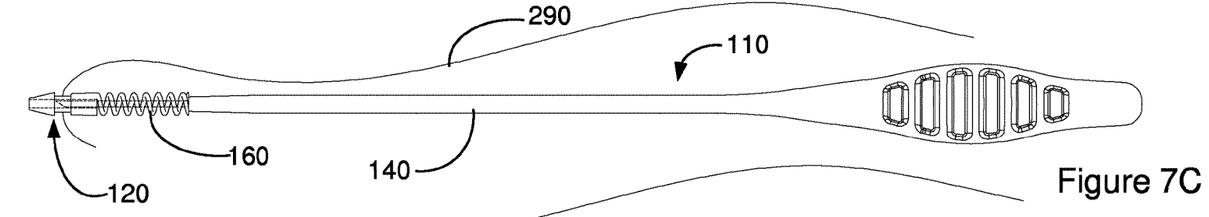
Figure 7D:
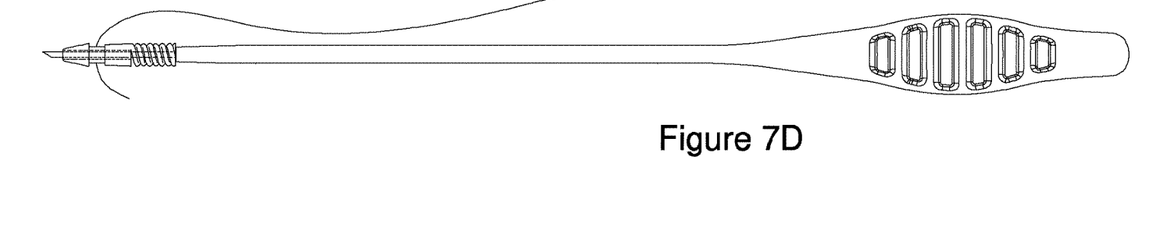

FIG. 7 shows a modification to the arrangement of FIG. 6. In this configuration the anchor incorporates the spring as opposed to the spring being provided as an element of the driver. In this arrangement the spring 160 is integrally formed as part of the anchor, it extends from the end surface 122 of the anchor. On loading the anchor to the driver, the spring 160 will initially be presented onto the sharpened tip 130 of the driver. The tip 130 will pass through the spring and then be received into the main body of the anchor. The length of the spring portion is selected such that on receipt and prior to compression of the spring, the sharpened tip will be shielded by the end portion 121 of the anchor. In use the system will operate as heretofore described.

While FIG. 7 shows an integrally moulded spring, it will be appreciated that a separately formed resilient element could be coupled to the anchor. It is important that the coupling arrangement is such that the two will not separate during use.

Figures 8A, 8B, 8C:
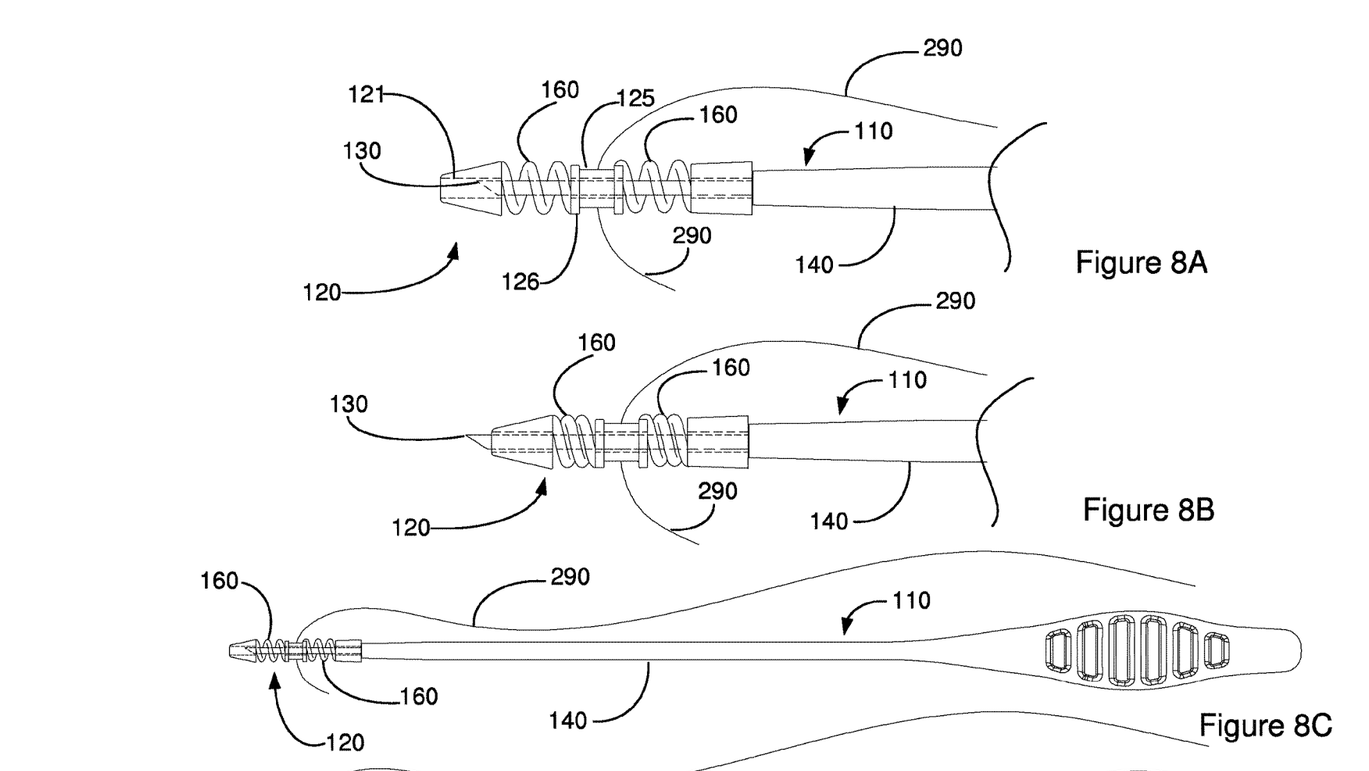
FIG. 8A-8D shows alternate geometries of a suture delivery system provided in accordance with the present teaching.
Figure 8D:
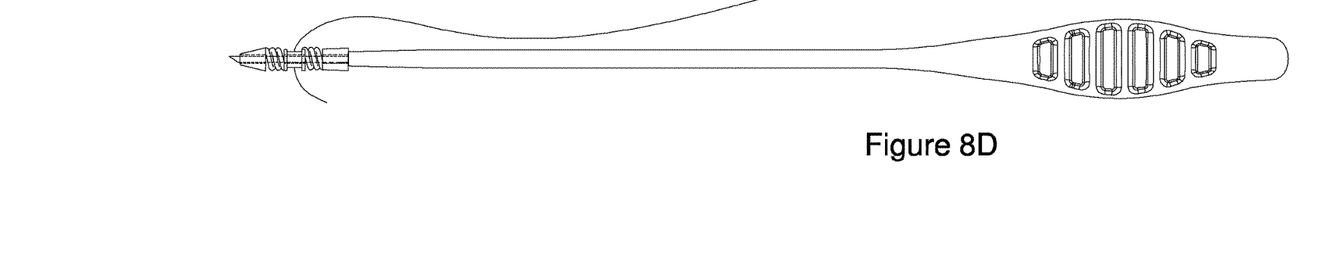

FIG. 8 shows a further modification to a spring/anchor combination. In this arrangement the spring is provided with two distinct portions 160 which are provided within the main body of the anchor 120. A first portion is provided between the chamfered end portion 121 and the step 125. A second portion is provided between the step and the end surface 122 of the anchor. By splitting the spring into multiple components and disposing them within the main body of the anchor it is possible to provide the same level of biasing force that could be achieved with a single spring-the arrangement of FIG. 7. However the arrangement of FIG. 8 could be advantageous as the suture 290 will still be coupled to the anchor 120 at a mid point or centre of mass of the anchor and will therefore allow the anchor to hang with symmetry—the desired T-bar configuration. This could be difficult in the arrangement of FIG. 7 where one side of the anchor (that incorporating the spring) will be heavier and have a greater length than the other.

It will be appreciated that the examples heretofore are of a delivery system used for the delivery of anchors within an abdominal cavity. It will be appreciated that the anchors of these examples serve a dual function—the primary function being when deployed as anchors. The secondary function is that they, or part of elements used to house the anchors during delivery of the anchor to the abdominal cavity, serve to shield the sharpened end tip 130, 330 of the driver. In the period of delivery of the anchors through the abdominal wall an external force is applied onto the anchor to effect a movement away from the tip to expose the tip. In the absence of this force the anchor is biased by the spring to operably cover or shield the tip. This may be considered a sheathed configuration. It will be appreciated therefore that the delivery system incorporates an integrated shield that is normally biased to cover or otherwise prevent a sharpened tip from causing inadvertent damage but which is moveable relative to the tip to allow the tip project and come into contact with the abdominal wall.

Where the driver is used to directly pass the anchor through the abdominal wall it is preferable that the driver has a degree of rigidity such that it will not flex during the presentation to and through the abdominal wall. In other configuration where the driver is for example presented through a guide channel it may be necessary for all or part of the driver body to have a degree of resilience or flex to allow it adopt to the contours of the guide channel. These two forms of driver may be collectively known as rigid or flexible drivers and within the context of the present teaching it is not intended to limit to any one form of driver—except as may be deemed necessary in light of a specific application of use.

While preferred arrangements have been described in an effort to assist in an understanding of the teaching of the present invention it will be appreciated that it is not intended to limit the present teaching to that described and modifications can be made without departing from the scope of the invention.

It will be appreciated that the exemplary arrangements or examples of devices have been described with reference to the Figures attached hereto. Where a feature or element is described with reference to one Figure, it will be understood that the feature or element could be used with or interchanged for features or elements described with reference to another Figure or example. The person of skill in the art, when reviewing the present teaching, will understand that it is not intended to limit the present teaching to the specifics of the illustrated exemplary arrangements as modifications can be made without departing from the scope of the present teaching.

The words comprises/comprising when used in this specification are to specify the presence of stated features, integers, steps or components but does not preclude the presence or addition of one or more other features, integers, steps, components or groups thereof.

The invention claimed is:

1. A surgical anchor delivery system comprising:
a driver comprising a main body portion and a needle end portion, the needle end portion having a tip; and
a removable hollow anchor defining a lumen, the anchor being separately formed from the driver and operably being fully removable from the driver on delivery of the anchor through an abdominal wall;
wherein the tip of the needle end portion is dimensioned to project through the lumen of the anchor such that the anchor is located on the driver between the tip of the needle end portion and the main body portion of the driver;
the anchor being moveable relative to the needle end portion so as to project beyond the tip of the needle end portion to cover and prevent contact with the tip, thereby shielding the tip during delivery of the anchor;
wherein the system further comprises a spring acting on the anchor to operably bias the anchor in a direction towards the tip, such that in the absence of an external force acting on the anchor, the anchor shields the tip such that the system has a first configuration during passage of the anchor through the abdominal wall wherein the needle end portion is exposed by application of the external force to bias the anchor such that it moves away from the needle end portion and a second configuration subsequent to passage of the anchor through the abdominal wall wherein the needle end portion is shielded by movement of the anchor towards the tip, and wherein on delivery of the anchor through the abdominal wall, a withdrawal of the driver disengages the anchor from the driver.

2. The system of claim 1 wherein provision of an external force onto the anchor causes the anchor to move on a direction away from the tip, thereby operably compressing the spring.

3. The system of claim 1 comprising a flexible driver.

4. The system of claim 1 wherein the spring is over-moulded onto or adhesively coupled onto a driver of the delivery system.

5. The system of claim 1 wherein the anchor is coupled to suture.

6. The system of claim 1 wherein the anchor comprises one or more projections on its outer surface to assist in a cutting of a fascia layer during use of the system.

7. The system of claim 1 wherein the tip of the needle end portion is sharpened to allow a piercing of the tissue as necessary.

8. The system of claim 1 comprising a driver and wherein a head portion of the driver includes a textured outer surface or bulbous head portion which provides improved grip to the user of the driver.

9. The system of claim 1 wherein the driver and tip of the needle end portion have a triangular profile which operably align with triangular features provided on an exterior surface of the anchor.

10. The system of claim 1 wherein the spring is formed separately to, but operably coupled, to the anchor.

11. A surgical method comprising:
making an incision in an abdominal wall and providing a system as claimed in claim 1,
presenting the system to tissue,
increasing a force on the system so as to cause the anchor to retract away from the needle end portion and allow the needle end portion to come into contact and pass through the tissue;
presenting the needle end portion into an abdominal cavity which automatically causes the anchor to move relative to the needle end portion and shield the needle end portion.

* * * * *